US008778002B2

(12) United States Patent
Moy

(10) Patent No.: US 8,778,002 B2
(45) Date of Patent: Jul. 15, 2014

(54) METHODS OF LIGHT TREATMENT OF WOUNDS TO REDUCE SCAR FORMATION

(76) Inventor: Ronald L. Moy, Beverly Hills, CA (US)

(*) Notice: Subject to any disclaimer, the term of this patent is extended or adjusted under 35 U.S.C. 154(b) by 269 days.

(21) Appl. No.: 13/049,748

(22) Filed: Mar. 16, 2011

(65) Prior Publication Data

US 2011/0230870 A1 Sep. 22, 2011

Related U.S. Application Data

(60) Provisional application No. 61/314,560, filed on Mar. 16, 2010.

(51) Int. Cl.
*A61N 5/06* (2006.01)

(52) U.S. Cl.
USPC .............................. 607/89; 607/88

(58) Field of Classification Search
USPC ................ 128/898; 606/8–9; 607/88–89
See application file for complete search history.

(56) References Cited

U.S. PATENT DOCUMENTS

| 5,334,191 | A | 8/1994 | Poppas et al. |
| 5,409,479 | A | 4/1995 | Dew et al. |
| 5,505,726 | A | 4/1996 | Meserol |
| 6,402,008 | B1 | 6/2002 | Lucas |
| 7,052,167 | B2 | 5/2006 | Vanderschuit |
| 8,123,744 | B2 | 2/2012 | Podhajsky |
| 2001/0037120 | A1* | 11/2001 | Northrup et al. ............... 606/153 |
| 2003/0204182 | A1 | 10/2003 | Ahle et al. |
| 2005/0015121 | A1 | 1/2005 | Molina |
| 2005/0049582 | A1 | 3/2005 | Debenedictis et al. |
| 2005/0192650 | A1 | 9/2005 | Martel |
| 2007/0233209 | A1 | 10/2007 | Whitehurst |
| 2008/0058783 | A1 | 3/2008 | Altshuler et al. |
| 2009/0069741 | A1* | 3/2009 | Altshuler et al. ............... 604/22 |
| 2009/0137996 | A1 | 5/2009 | Debenedictis |
| 2009/0254076 | A1* | 10/2009 | Altshuler et al. ............... 606/33 |
| 2011/0230817 | A1 | 9/2011 | Moy |

FOREIGN PATENT DOCUMENTS

WO WO 2005/099369 10/2005

OTHER PUBLICATIONS

"Twenty-five years of active laser prevention of scars: What have we learned?" F. M. Leclère & Serge R. Mordon Journal of Cosmetic and Laser Therapy, 2010; 12: 227-234.*
"Low-Level Laser Therapy (LLLT) Efficacy in Post-operative Wounds" Herascu et al. Photomedicine and Laser Surgery vol. 23, No. 1, 2005.*
"Photodynamic therapy in dermatology" Kalka et al. J Am Acad Dermatol vol. 42, No. 3 2000.*
Steven S. Greenbaum and Mark G. Rubin. "Surgical Pearl: The high-energy pulsed carbon dioxide laser for immediate scar resurfacing" Journal of the American Academy of Dermatology Jun. 1, 1999 (vol. 40 issue 6 pp. 988-990).*

(Continued)

*Primary Examiner* — Bill Thomson
*Assistant Examiner* — Nathan J Jenness
(74) *Attorney, Agent, or Firm* — Knobbe Martens Olson & Bear, LLP

(57) ABSTRACT

A method of reducing scar formation associated with a skin wound includes providing an electromagnetic energy source, delivering energy from the electromagnetic energy source to opposing edges of a skin wound, and sealing the wound after delivering the energy. The electromagnetic energy source can include a laser, such as a fractional laser, including a fractional $CO_2$ laser. Handpieces configured to reduce scar formation include one or more of a tissue eversion system, a medication delivery system, and a wound sealing system.

19 Claims, 13 Drawing Sheets

(56) References Cited

OTHER PUBLICATIONS

Thomas E. Rohrer and Steven J. Ugent. "Evaluating the efficacy of using a short-pulsed erbium:YAG laser for intraoperative resurfacing of surgical wounds" Lasers in Surgery and Medicine 30: 101-105 (2002).*

Alexandre Capon et al. "Scar Prevention Using Laser-Assisted Skin Healing (LASH) in Plastic Surgery" Aesthetic Plastic Surgery 34: 438-446 (2010); published online Jan. 28, 2010.*

International Search Report and Written Opinion from (PCT/US2011/028730), dated Jun. 28, 2011.

* cited by examiner

METHODS OF LIGHT TREATMENT OF WOUNDS TO REDUCE SCAR FORMATION

CROSS-REFERENCE TO RELATED APPLICATIONS

The present application claims priority from U.S. Provisional No. 61/314,560, filed Mar. 16, 2010, which is expressly incorporated by reference in its entirety.

BACKGROUND OF THE INVENTION

1. Field of the Invention

The invention relates to methods of using electromagnetic energy to enhance wound healing and to minimize or prevent scar formation.

2. Description of the Related Art

Fractional electromagnetic energy is used to treat a variety of skin and tissue conditions and pathologies. Such treatments typically employ light-based devices such as lasers and RF devices to deliver energy to the epidermis and/or the dermis of a subject's skin. Controlled applications of light energy penetrate to various depths of the skin. Energy penetration results in localized heat deposition through the subsurface of the skin as well as localized thermal damage within the epidermis and/or dermis, depending upon the depth of penetration. Thermal damage within the skin at treatment sites and, in some cases throughout the surrounding adjacent tissue, causes immediate and long-term, natural healing effects within the affected tissue. Such natural healing effects include collagen contraction and stimulation of collagen formation, which result in a macro effect of collagen regeneration throughout the underlying skin layers.

A number of skin treatments are possible with lasers and RF devices. For example, such device may be used for relatively superficial treatments of the epidermal layers for treatment of fine lines, skin texture, pigmentation (dyschromia) and sun damage, as well as deeper treatments of the epidermal and dermal layers for treatment of deep wrinkles and scars. Non-limiting examples of such devices are described in U.S. Pat. Nos., 6,328,733; 6,451,010; 6,758,845; and 7,438,712, which are all expressly incorporated by reference herein in their entireties.

However, a need remains for a safe, effective electromagnetic energy-emitting devices and methods to enhance wound healing and reduce scar formation.

SUMMARY OF THE INVENTION

In one embodiment, a method of reducing scar formation associated with a skin wound, includes: providing an electromagnetic energy source; delivering energy from the electromagnetic energy source to opposing edges of a skin wound; and sealing the wound after delivering the energy. The electromagnetic energy source can include a laser, a fractional laser, or a CO2 laser.

The method can include scanning a pattern of treatment spots over a treatment area around the skin wound. In one embodiment, the treatment area is circular with a diameter in a range of from about 1.3 mm to about 20 mm, or about 10 mm. The delivering energy can include delivering laser light having a wavelength in a range of from about 9400 nm to about 11100 nm, delivering laser light in a range of from about 5.2 J/cm2 to about 445 J/cm2, delivering laser light having a pulse width in a range of from about 20 microseconds to about 1000 microseconds, delivering laser light having a spot density in a range of from about 5% to about 100%, and/or creating a plurality of channels in the skin around the wound, each channel having a depth of about 40 microns to about 1500 microns.

The sealing can include suturing the wound closed, delivering a surgical staple to skin near the skin wound to close the wound, delivering a tissue glue to the skin wound to close the wound, and/or tissue welding.

The method can also include everting the wound prior to delivering energy from the electromagnetic energy source. The method can also include delivering additional energy from the electromagnetic energy source to opposing edges of the skin wound after sealing.

In another embodiment, a method of reducing scar formation associated with a skin wound includes: providing a laser system comprising a laser and a scanning handpiece optically coupled to the laser, the scanning handpiece configured to direct laser energy from the laser to a treatment area on a patient's skin to form a plurality of spots on the patient's skin within the treatment area; aligning an aiming beam emitted from said handpiece with respect a wound on the patient's skin; activating the laser and handpiece to direct the laser energy from the laser to the treatment area on the patient's skin to form the plurality of spots on the patient's skin, wherein said treatment area comprises at least first and second portions spaced apart from each other and located on opposite sides of said aiming beam such that at least some of said laser energy is delivered to skin near the wound's edges; and sealing the wound after scanning said laser beam within the treatment area. The first and second portions can be spaced apart from each other by about a width of the wound or by at least the width of the wound. In some embodiments, the spacing between the first and second portions is changed based upon the width of the wound. For example, in some embodiments, the spacing between the first and second portions is changed automatically based upon the width of the wound, for example, by a sensor located in the handpiece that optically or mechanically senses the wound's width.

In another embodiment, an electromagnetic energy system configured to reduce scar formation associated with a skin wound includes: an electromagnetic energy source configured to generate an electromagnetic energy beam having a plurality of beam parameters; an optical energy conduit having a proximal and a distal end, the optical energy conduit coupled to the electromagnetic energy source at the proximal end; a handpiece coupled to the distal end of the optical energy conduit; and a memory, comprising predetermined, stored values of the plurality of beam parameters, the predetermined values of the beam parameters configured to reduce scar formation associated with a skin wound.

The beam parameter can include a pulse width, a treatment area size, a treatment area shape, a spot size, a power level, a fluence, and/or a penetration depth. The electromagnetic energy source can include a laser, a CO2 laser, and/or a fractional laser. The electromagnetic energy system can also include an aiming beam configured to be aligned with a wound prior to delivering energy from the electromagnetic energy source to a treatment area near the wound. In one embodiment, the treatment area is spaced a predetermined distance from the aiming beam. The aiming beam can be formed as a line or a curve.

In yet another embodiment, a handpiece for delivering electromagnetic energy to a tissue treatment site to reduce scar formation associated with a wound at the treatment site includes: a housing; a connector attached to a proximal end of the housing; a scanning system located at least partially within the housing and configured to receive electromagnetic energy from an electromagnetic energy source and deliver the electromagnetic energy within a treatment area at a treatment site on a patient's skin as a user-controllable pattern of spots within the treatment area; and a tissue eversion system protruding at least partly beyond a distal end of the housing, the tissue eversion system configured to evert tissue around a wound at the treatment site prior to delivering the electromagnetic energy.

The tissue eversion system can include first and second legs, wherein a distance between the first and second legs is controllable by a user. The handpiece can also include a sensor configured to determine a spacing between the first and second legs. The handpiece can control a diameter of the treatment area in response to the distance between the first and second legs.

The legs can include a material that doesn't reflect a substantial portion of electromagnetic energy incident upon the leg. The material can include a non-reflective coating. The handpiece can also include a medication delivery system configured to deliver a medication to the treatment site during delivery of the electromagnetic energy. The handpiece can also include a wound sealing system configured to seal the wound after delivery of electromagnetic energy. The handpiece can also include a control located on housing configured to activate the tissue eversion system.

In another embodiment, a handpiece for delivering electromagnetic energy to a tissue treatment site to reduce scar formation associated with a wound at the treatment site, the handpiece includes: a housing; a connector attached to a proximal end of the housing; a scanning system located at least partially within the housing and configured to receive electromagnetic energy from an electromagnetic energy source and deliver the electromagnetic energy within a treatment area at a treatment site on a patient's skin as a user-controllable pattern of spots within the treatment area; and a medication delivery system located at least partially within the housing and configured to deliver a medication to tissue around a wound at the treatment site during delivery of the electromagnetic energy.

The medication delivery system can include a removable cartridge containing the medication. The medication can include one or more of a drug, a steroid, Cortisone, 5-fluorouracil, an anti-cancer drug, an antimycotic, an anti-fungal drug, and a liposome. The medication delivery system can include a nozzle configured to spray the medication towards the treatment site. The handpiece can also include a control located on the housing, the control configured to activate the medication delivery system.

In yet another embodiment, a handpiece for delivering electromagnetic energy to a tissue treatment site to reduce scar formation associated with a wound at the treatment site includes: a housing; a connector attached to a proximal end of the housing; a scanning system located at least partially within the housing and configured to receive electromagnetic energy from an electromagnetic energy source and deliver the electromagnetic energy within a treatment area at a treatment site on a patient's skin as a user-controllable pattern of spots within the treatment area; and a wound sealing system located at least partially within the housing and configured to hold closed a wound at the treatment site after delivery of the electromagnetic energy.

The wound sealing system can include a stapler, a tissue glue, and/or a tissue welding system. The handpiece can also include a control located on the housing, the control configured to activate the wound sealing system.

DETAILED DESCRIPTION OF THE PREFERRED EMBODIMENT

Fractional light treatments of skin and tissue include microablative techniques that employ, for instance, laser radiation to ablate microchannels within the skin layers at controlled depths and widths. Surrounding tissue adjacent and between microchannels does not experience thermal damage along the microchannels, although thermal effects are exhibited throughout the layers of surrounding tissue. This results in the noted macro effect, discussed above, throughout the skin layers and advantageous long-term effects on the structure of the skin layers.

Figure 1:
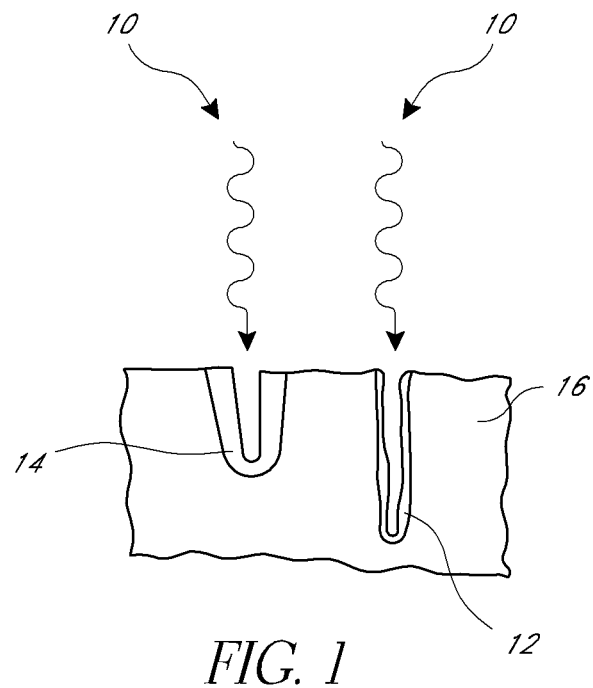
FIG. 1 is a cross-sectional view of tissue that includes micro channels formed a result of a fractional treatment using a microablative technique.

Referring to FIG. 1, microablative techniques control depths and widths of microchannels through the mode of laser radiation employed whether as continuous or pulsed light radiation. Typically pulsed light 10 is employed to create narrow and deep microchannels 12 penetrating to a certain depth in the subsurface tissue including the dermal layers, as well as to create comparatively superficial and wide microchannels 14 penetrating into the epidermal layers and to a significantly shallower depth into the dermal layers of the subject's skin 16. In addition, microablative techniques control microchannel structure through, for instance, the selection of laser radiation power, wavelength, energy density or fluence (Joules/cm2), pulse width, pulse duration, pulse rate (pulses/sec), and the shape and size of radiation treatment areas.

Figure 2:
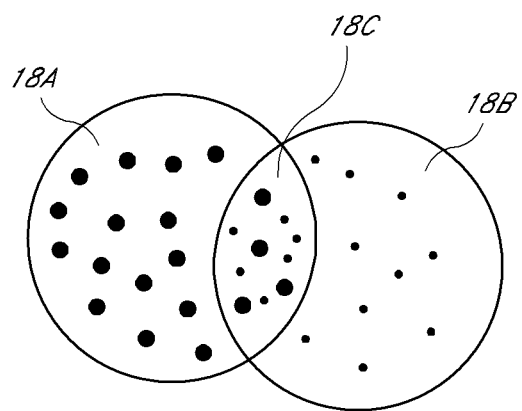
FIG. 2 is a top view of different patterns of radiation treatment "spots" applied to skin treatment areas, which creates patterns of micro channels through subsurface tissue, such as shown in FIG. 1.

Referring to FIG. 2 and with further reference to FIG. 1, microablative techniques typically apply radiation treatment to the skin as a pattern 18A and 18B of treatment areas or "spots." The term "spots" as used in this specification includes any areas along the skin at which radiation energy penetrates into subsurface tissue or one or more layers of the skin to create micro-ablated channels. As shown in FIG. 1, various microchannel structures 12 and 14 may be created with the selection of various parameters that facilitate microablation. For instance, selection of spot shape or, more particularly, selection of spot diameter may be used to control the width of the resulting micro channel. Selection of the radiation energy density may be used to control the ablation rate or depth of the resulting microchannel.

As shown in FIG. 2, a given spot treatment pattern 18A and 18B may include a specific spot diameter and a specific density of spots in a scanned treatment area. One scan pattern 18A may include spots having comparatively wide diameters with a comparatively high spot density, while another scan pattern 18B may include spots having comparatively narrower diameters and comparatively lower spot density. The area or volume of the required or desired healing zone may be adjusted by varying the density of the treatment spots within a given pattern. Spot size and spot density of a given treatment pattern thereby produce the pattern of light radiation that creates and distributes multiple microchannels throughout subsurface tissue in the given pattern 18A and 18B. In some methods, one or more treatment patterns 18A and 18B may be employed to produce an overlapping treatment pattern 18C that produces different micro channel structures 12 and 14 and thereby provides one or more microablative effects throughout the layers of skin.

Microablative techniques for fractional light treatment often employ fractional CO2 lasers that may emit radiation at wavelengths of up to 10,600 nm. In particular, the patterned light radiation as described above may be delivered to treatment areas at high fluences (e.g., high energy density per laser pulse) for facial skin treatment applications and lower fluences (e.g., low energy density per laser pulse) for non-facial skin treatment applications. High energy density per pulse enables deep penetration, for instance, into the dermis of facial skin for immediate collagen contraction and stimulation of collagen formation.

In one embodiment, microablative techniques employing the patterned treatment spots described above apply radiation energy to only a small area or volume of subsurface tissue relative to the overall scanned area of skin. A relatively broad treatment area of the skin may be scanned with a radiation delivery device. Yet, the delivery device emits radiation energy in a given pattern of treatment spots that applies energy to only a fraction of the subsurface tissue underlying the scanned area of skin. Radiation energy is absorbed by the skin and creates microchannels without exposing the surrounding tissue. As mentioned, the ablative techniques of micro channel formation create healing effects throughout the surrounding adjacent tissue that results in an advantageous macro effect throughout the subsurface tissue.

In addition to CO2 lasers, fractional light treatment using microablation techniques may also employ iridium lasers and other lasers. Fractional light treatments also include procedures that may use non-ablative techniques that may employ general Nd:YAG and other lasers operative in non-ablative modes, as well as arrays of RF needle electrodes.

Figure 3:
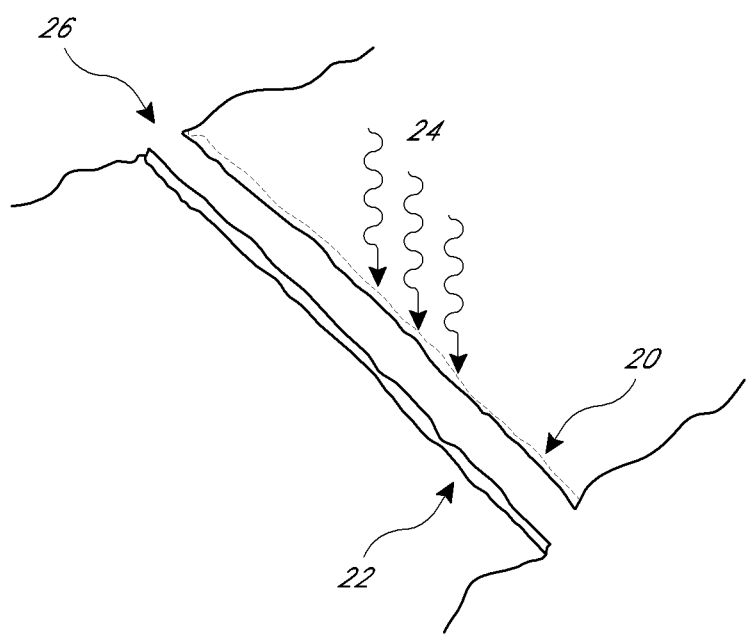
FIG. 3 is a top view of tissue illustrating one embodiment of a method of pretreatment of a surgical incision site prior to suturing an incision.

Referring to FIG. 3, in one embodiment, a method of intraoperative treatment of surgical wounds with fractional microablative light radiation reduces or eliminates subsequent scar formation after surgical intervention. Tests employing the fractional microablative light treatments discussed above in the context of surgical wound healing indicate significant reductions in scar formation. More particularly, test results show that fractional microablative light treatments of surgical incisions with light radiation before suturing results in a significant decrease in subsequent scar formation.

In one configuration of the method, a fractional CO2 laser was employed to deliver pulsed light energy 24 to each of the edges 20 and 22 of a surgical incision site 26 in facial tissue at the time of excision and prior to suturing. The surgical sites 26 were a minimum of about 2 cm in length. The treatment spot was about 10 mm. The treatment spot included an overlap between adjacent treatment spots of about 5 mm.

Other parameters of the laser beam produced with the fractional CO2 laser employed in the surgical wound pretreatment include light radiation having wavelengths in a range of from about 9,400 nm to about 11,100 nm, and energy density or fluence in a range of from about 5.2 Joules/cm2 to about 445 Joules/cm2 that was delivered with a pulse width in a range of from about 20 μs to about 1000 μs.

The treatment area can include about 1.3 mm to 20 mm of scan area and further included a spot density of between 5% and 100%. A penetration depth is estimated to be in the range of from about 40 μm per pulse to about 1500 μm per pulse.

One study performed according to one embodiment of the invention included ten Mohs micrographic surgery patients. Surgical incision sites were treated intraoperatively with a fractional CO2 laser in a randomized split fashion whereby half of a given incision site was treated with microablative light treatment and the remaining half of the incision site was left untreated before the incision site was sutured. The patients were seen and the incisions were photographed within one week of surgery and thereafter within two to three months of surgery. Scar questionnaires were completed at that time. Three physicians served as blinds to evaluate and rate the incision photographs.

The results indicate that eight of the ten patients had a significant improvement in the half of the incision sites that were treated with the fractional CO2 laser energy. Excellent agreement between patient observations and the blind physician ratings occurred.

The results indicate that the fractional CO2 treatment of the incision edges 20 and 22 at the time of excision, and prior to suturing of the incision, is significantly effective for minimizing the appearance of subsequent scar formation compared to the control surgical sites that did not receive such pretreatment.

The results further suggest that applications of high fluences of CO2 light energy to facial wounds enhance wound healing and help to reduce scar formation subsequent to surgical procedures.

The results also suggest broader applications of fractional CO2 light treatment to reduce scar formation after surgical intervention of non-facial tissue. In these cases, the fractional CO2 light treatment may be delivered at lower fluences. In addition, the results suggest that applications of fractional CO2 light treatment for non-surgical wound healing of both facial and non-facial tissue may be effective.

The therapeutic methods described herein may be performed with a variety of electromagnetic energy-emitting devices, including lasers, intense pulsed light, radiofrequency (RF) energy sources, as well as others. Indeed, iridium, erbium (e.g., Er:YAG and/or Er, Cr:YSGG), neodymium (e.g., Nd:YAG), and a variety of solid-state or diode laser devices may be employed to delivery light energy to surgical and non-surgical wounds to enhance healing and to help to minimize or prevent consequent scar formation according to any one or more of the methods discussed herein.

The invention also anticipates that other non-ablative light energy based treatments may be employed and may be effective fractional light treatments for enhancing surgical and non-surgical wound healing and for minimizing scar formation. For example, any laser configured for operating in a non-ablative fractional mode may be effective. Other electromagnetic-energy-based devices, such as RF electrode needles, may provide effective results, as well.

Figure 4:
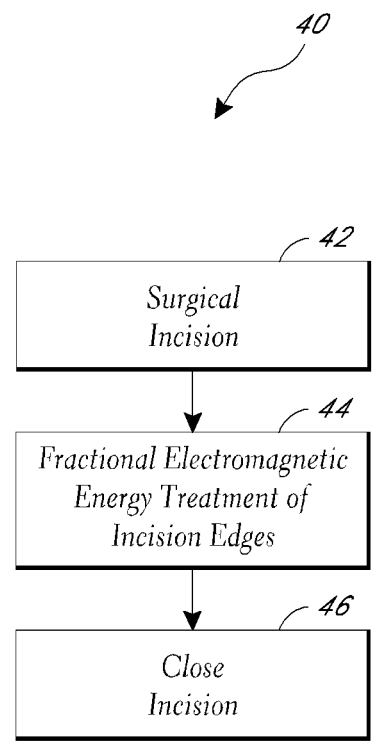
FIGS. 4 and 5 are flow charts illustrating methods of treating wounds to enhance healing and reduce or prevent scar formation.

Another embodiment of a method of enhancing healing and minimizing or preventing scar formation is illustrated in FIG. 4. The method 40 begins by performing a surgical incision at block 42. The incision may be performed using any of a variety of techniques and with any of a variety of devices, including a scalpel or laser. At block 44, electromagnetic energy is delivered to the margins of the tissue located at the incision site. For example, electromagnetic energy may be delivered to the edges of tissue (e.g., skin) on opposite sides of an incision.

The electromagnetic energy can be delivered with a scanning handpiece that scans a treatment beam over a treatment area and delivers a sequence of overlapping, abutting, and/or spaced-apart energy spots to the treatment area. In one embodiment, the electromagnetic energy source includes a fractional energy source, which spaces treatment spots apart from one another, for example, in the manner illustrated above with respect to FIGS. 1 and 2.

The method 40 proceeds to block 46, during which the clinician closes the surgical wound. For example, at block 46 the clinician may suture, staple, glue, or weld the treated tissue to close the surgical wound. Optionally, the method can further include an additional block (not shown), during which the clinician delivers a subsequent electromagnetic energy treatment to the closed surgical wound.

Figure 5:
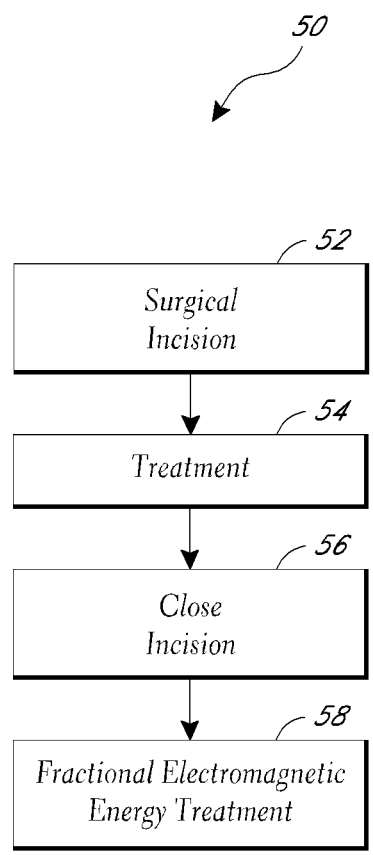

Another embodiment of a method of enhancing healing and minimizing or preventing scar formation is illustrated in FIG. 5. The method 50 begins by performing a surgical incision at block 52. The incision may be performed using any of a variety of techniques and with any of a variety of devices, including a scalpel or laser. At block 54, a surgical procedure is performed. For example, at block 54, a growth, lesion, or tumor is removed from the patient's body. The surgical treatment may include removing a portion of the patient's skin and/or removing a tissue mass from beneath the patient's skin. The method 40 proceeds to block 56, during which the clinician closes the surgical wound. For example, at block 58 the clinician may suture, staple, glue, or weld the treated tissue to close the surgical wound. At block 58, electromagnetic energy is delivered to the margins of the tissue located at the incision site. For example, electromagnetic energy may be delivered to the edges of tissue (e.g., skin) on opposite sides of the incision.

The electromagnetic energy can be delivered according to any of the methods described herein with a scanning or a non-scanning handpiece. A scanning handpiece typically includes one or more movable optics, such as a spinning mirror, that scans a treatment beam over a treatment area while the handpiece is held stationary at a treatment location on the patient's skin. The scanning treatment beam results in a sequence of overlapping, abutting, and/or spaced-apart spots within the treatment area. The treatment spots are generally circular in shape, and can be delivered within a variety of treatment area shapes and sizes, including square, triangular, rectangular, circular, hexagonal, trapezoidal, parallelogram, rhombus, linear, or annular shapes.

In one embodiment, the electromagnetic energy source includes a fractional energy source, which spaces treatment spots apart from one another, for example, in the manner illustrated above with respect to FIGS. 1 and 2.

Figure 6:
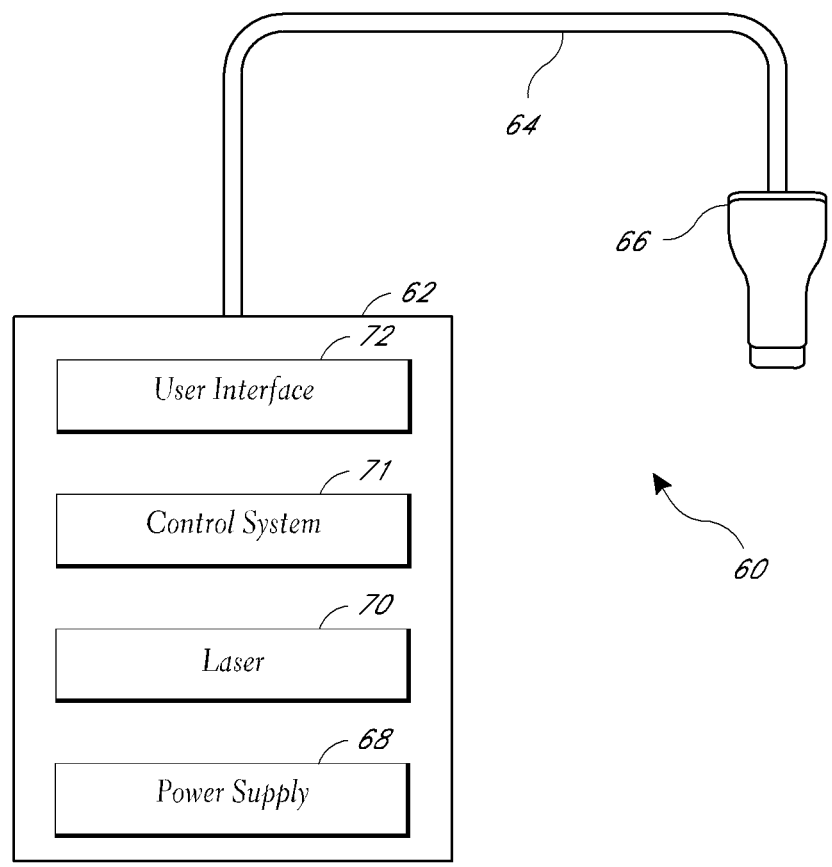
FIG. 6 is a schematic view of an electromagnetic energy source configured to perform any of the methods to enhance and reduce or prevent scar formation described herein.

One embodiment of a system 60 configured to perform methods of using electromagnetic energy to enhance wound healing and to minimize or prevent scar formation is illustrated in FIG. 6. The system 60 includes an electromagnetic energy source 62 that is coupled to a handpiece 66 (sometimes referred to as an adapter 66) by an energy conduit 64. The electromagnetic energy source 62 includes a power supply 68, a laser 70, a control system 71, and a user interface 72. A user controls the operation of the system 60 via the user interface 72.

In one embodiment, the laser 70 includes a CO2 laser that emits a beam of light having a wavelength of 10,600 nm. The laser 70 can operate in a pulsed or continuous mode, and deliver up to 240 W of power to a treatment site. The control system 71 includes a microprocessor and/or other electronic hardware and software to control system operation according to input received from the user interface 72. In one embodiment, the control system 71 includes a memory configured to store data or presets relating to one or more beam parameter settings. For example, the memory can store predetermined beam parameter setting values and it can store user-configurable beam parameter setting values. The beam parameter settings correspond to any of a variety of electromagnetic energy, light, and/or laser parameters, including but not limited to: pulse width, average power, peak power, duty cycle, energy, fluence, treatment area shape, spot density, spot size, depth of penetration, etc. The energy conduit 64 includes a waveguide, articulated arm, and/or fiberoptic delivery system to conduct electromagnetic energy from the energy source 62 to the handpiece 66.

The laser beam spot sizes can be controlled to have a variety of diameters by adjusting corresponding setting on the user interface 72. For example, the laser beam's spot sizes can be controlled to have a diameter of 120, 200, 1000, 1300, or 2000 μm. The handpiece 66 includes scanning optics to provide fractional lasing of the target tissue surface.

Figure 7:
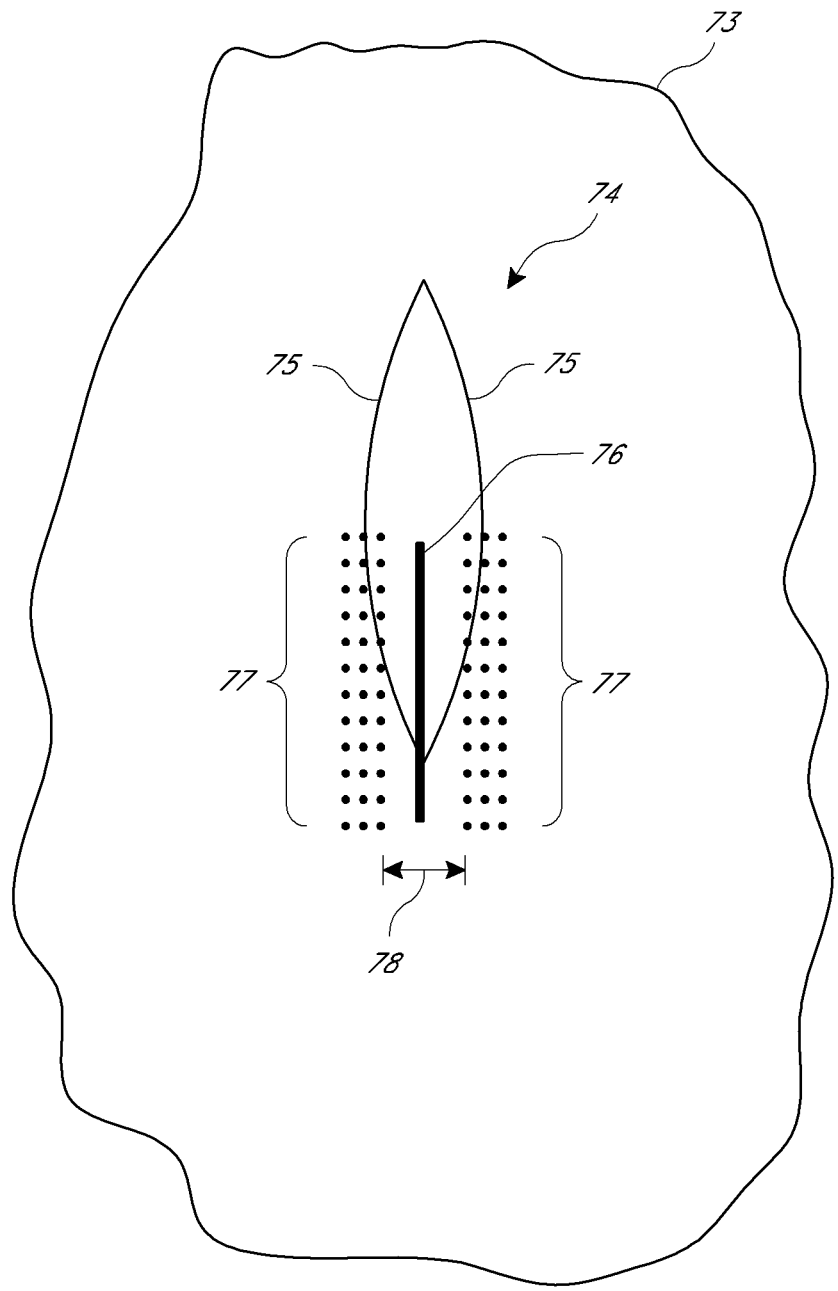
FIG. 7 is a top view of tissue treated with a fractional laser energy from the electromagnetic energy source of FIG. 6.

In one embodiment illustrated in FIG. 7, the handpiece 66 emits an alignment beam 76 of visible, non-therapeutic light (e.g., a spot, line, or curve from a red or green aiming beam, such as a laser, Helium Neon laser, diode laser, light emitting diode, etc.) to help the clinician align the therapeutic energy from the handpiece with a surgical wound 74 on the patient's skin 75. For example, the handpiece 66 can emit a visible line of light 76 that the clinician can center between the edges 75 of a surgical incision 74 prior to activating the laser 70 of the system 60.

The alignment beam 76 provides a reference point (or line) with respect to the treatment areas 77 of the therapeutic energy from the laser 70. For example, as illustrated in FIG. 7, the treatment areas can include two rectangular areas 77 spaced apart by a predetermined distance 78. The predetermined distance 78 can be selected by the clinician to deliver more energy to the patient's skin 75 and surgical wound's edges 75, and less energy to the tissue between the surgical wound's edges 75.

Figure 8:
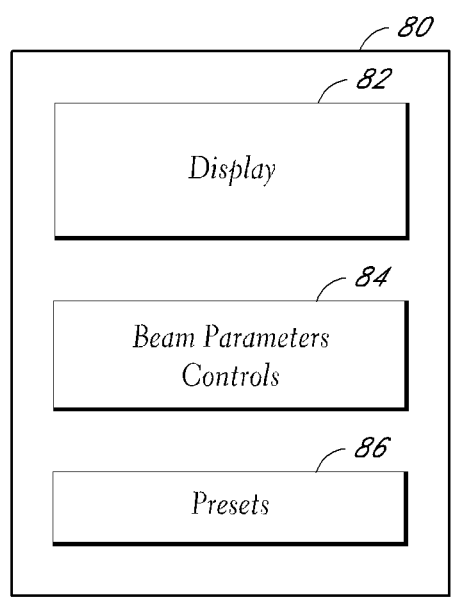
FIG. 8 is a schematic view of a user interface of the electromagnetic energy source of FIG. 6.

One embodiment of a user interface 80 is illustrated in FIG. 8. The user interface 80 includes a display area 82, beam parameter controls 84, and presets 86. The display area 82 indicates to the user the current status of the system, such as whether it is ready to be activated, whether it is emitting electromagnetic energy, and beam parameter setting, as well as other useful clinical information. The beam parameter controls 84 allow the user to control the therapeutic energy beam emitted from the system 60. For example, the beam parameter controls 84 can allow the user to control the power delivered to the patient's tissue, the shape and size of the treatment area, the size of the spots delivered by the handpiece 66, the width of each optical pulse, the temporal and spatial spacing between pulses, the energy density delivered to the patient's tissue, the depth of penetration, the width or diameter of the beam spots, etc.

In one embodiment, the beam parameter controls 84 also allow the user to control the shape, size, color and/or brightness of the alignment beam 78 (as discussed above with respect to FIG. 7). The beam parameter controls 84 can also allow the user to control the number of treatment areas 78 to be delivered by the system 60, as well as their shapes (e.g., rectangular, as illustrated in FIG. 7) and spacing 78.

The presets 86 are user-selectable configurations that correspond to a group of beam parameter controls relevant to a particular clinical therapy. For example, the user interface 80 can include a preset 86 corresponding to "Surgical Scar Reduction," which when selected would set one or more beam parameter controls to predetermined levels, such as the levels or settings discussed above. The preset 86 adjusts a combination of beam parameters to result in an overall system 60 setting that provides electromagnetic energy to enhance wound healing and to minimize or prevent scar formation.

Figure 9:
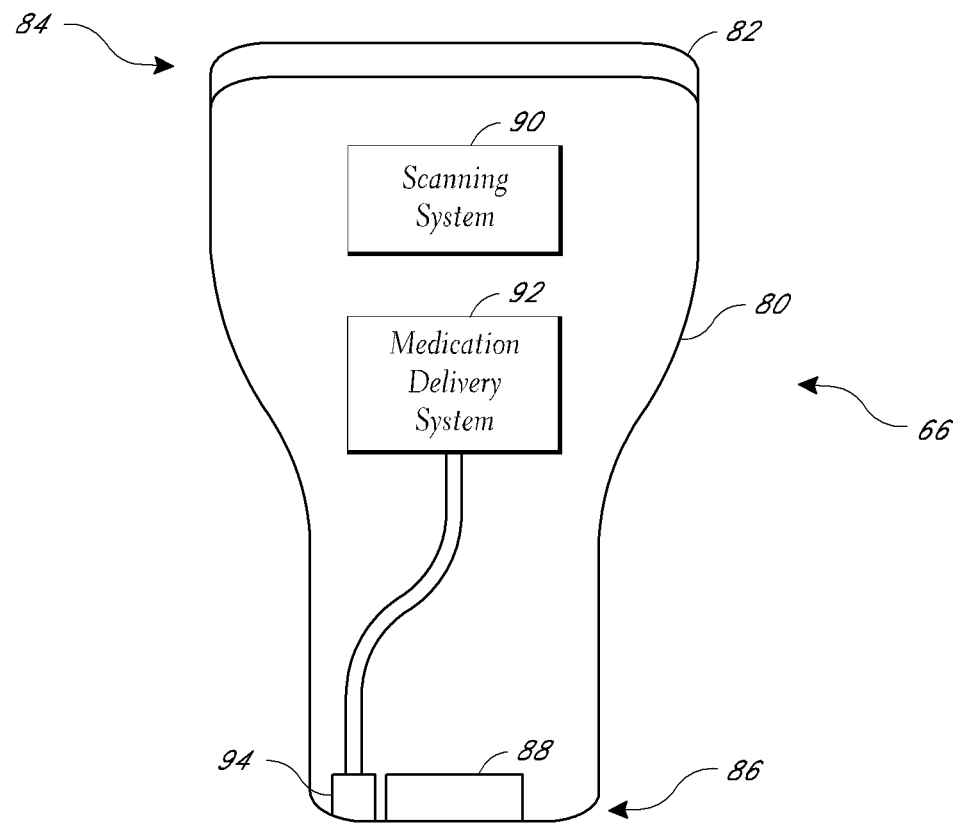
FIGS. 9 and 10 are schematic views of handpieces configured to deliver a medication, which are compatible with the electromagnetic energy source of FIG. 6.

One embodiment of a scanning laser handpiece 66 adapted to enhance wound healing and minimize or prevent scar formation is illustrated in FIG. 9. The handpiece 66 includes a housing 80 and a connector 82 at the handpiece's proximal end 84. The connector 82 allows the handpiece to be removably attached to an energy conduit, such as the energy conduit 64 of FIG. 6. An optical output 88 is located at the handpiece's distal end 86. The optical output 88 can include one or more of an aperture, lens, and window. The handpiece 66 includes a scanning system 90, which may include various lenses, mirrors, and motors to create a fractional treatment area on the patient's skin. The handpiece 66 also includes a medication delivery system 92 that is configured to deliver a medicament to a treatment site during treatment.

For example, the medication delivery system 92 can include a tubing, pump, spray or other device adapted to eject a liquid or cream from a handpiece output 94 to a treatment site on the patient's skin. The medication delivery system 92 can include a user-changeable cartridge, such as a single-use cartridge, that includes the medication.

The medication can include one or more of a drug, steroid, Cortisone, 5-fluorouracil, an anti-cancer drug, an antimycotic (e.g., anti-fungal) drug, or a liposome. Such substances can help with wound healing and scar reduction and prevention. In some embodiments, the flow rate of the medication is controlled in response to beam parameter controls 84 or presets 86 selected by the user. For example, in one embodiment, when the beam penetration depth, diameter, power, or fluence is increased, the medication delivery rate is increased, as well. Similarly, as these parameters are decreased, the medication delivery rate is decreased, as well.

The medication is delivered from the medication output 94 to the tissue treatment site before, during, and/or after deliver of electromagnetic energy. In some embodiments, the handpiece 66 includes a roller ball or cylinder, or a spatula arm that spreads the medication over the treatment area during and after treatment.

Figure 10:
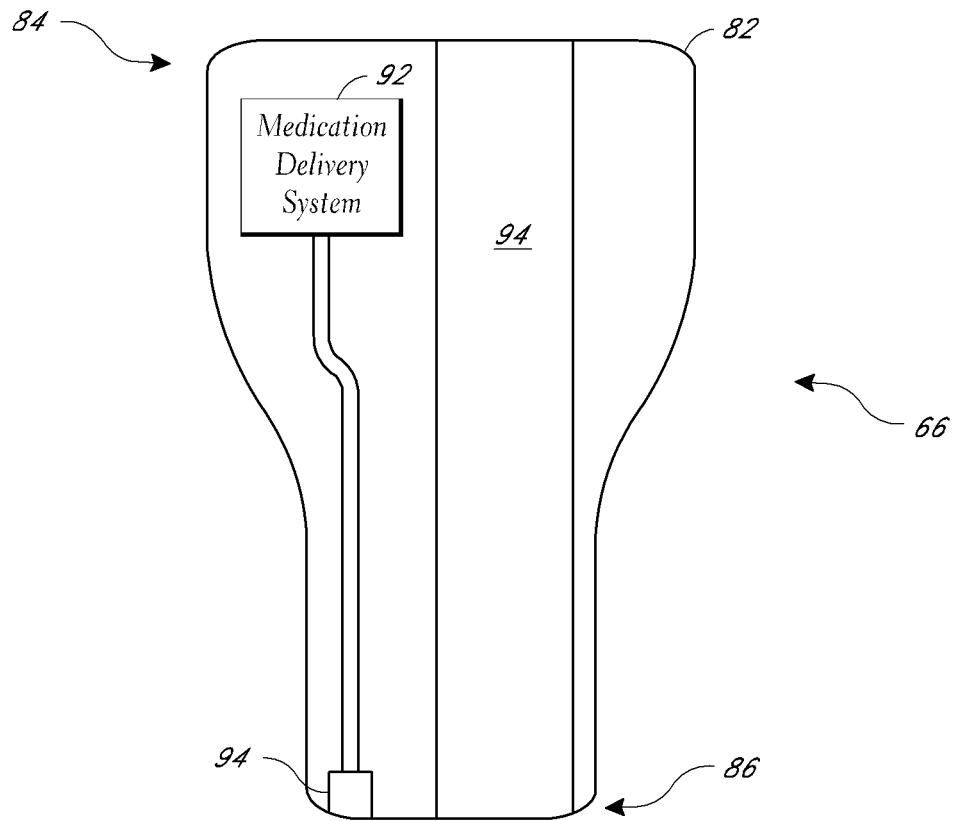

In another embodiment, as illustrated in FIG. 10, a handpiece 66 includes an optical path 94 instead of the scanning system 90 of FIG. 9. The optical path 94 can include a fiberoptic, a waveguide and/or stationary mirrors and lenses (stationary with respect to the handpiece 66), to direct electromagnetic energy, such as laser light, from the handpiece's proximal end 84 to its distal end 86.

Figure 11:
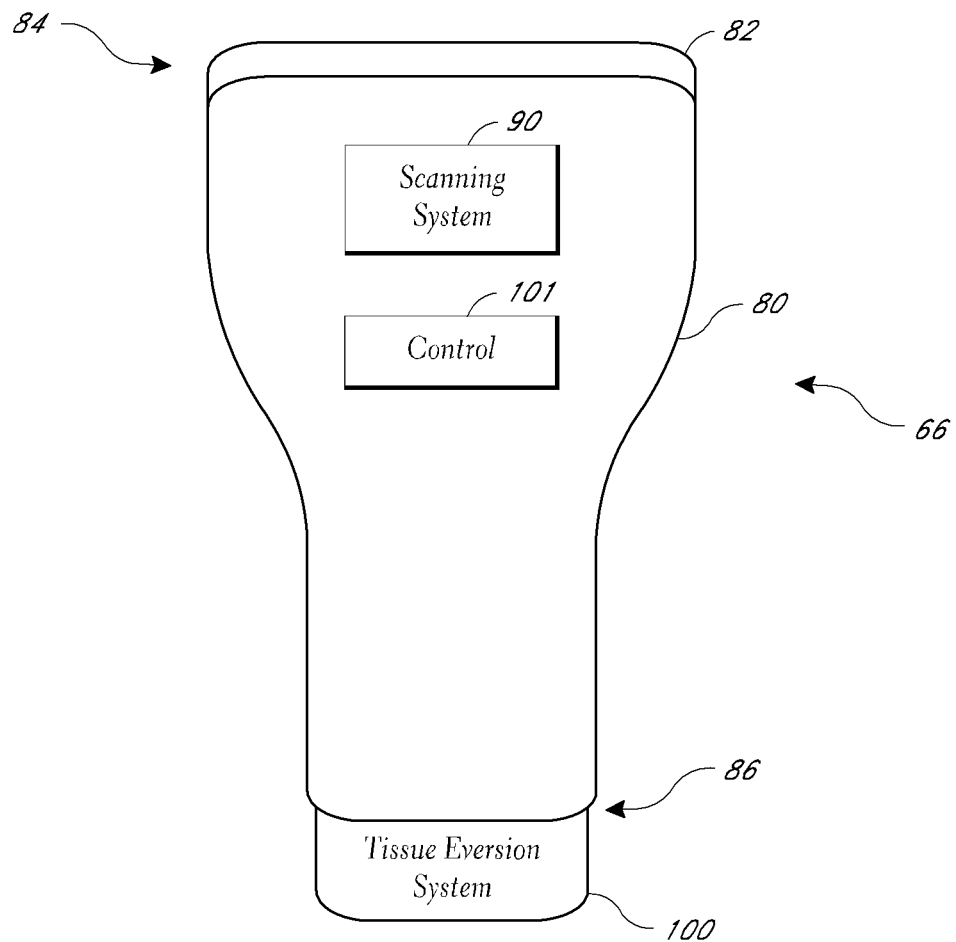
FIG. 11 is a schematic view of a handpiece configured to evert tissue before, during and/or after energy treatment, which is compatible with the electromagnetic energy source of FIG. 6.

FIG. 11 illustrates another embodiment of a handpiece 66 configured to enhance wound healing and reduce or prevent scar formation. The handpiece 66 includes a housing 80, connector 82, and scanning system 92, similar to those described above. However, the handpiece 66 of FIG. 11 also includes a tissue eversion system 100 and control 101 for tissue eversion activation. The tissue eversion system 100 bring opposing edges 114 of a surgical wound 112 together such that the skin 110 is in tension, and wound edges 114 press against or overlap one another, as shown in FIGS. 12-15.

Figure 12:
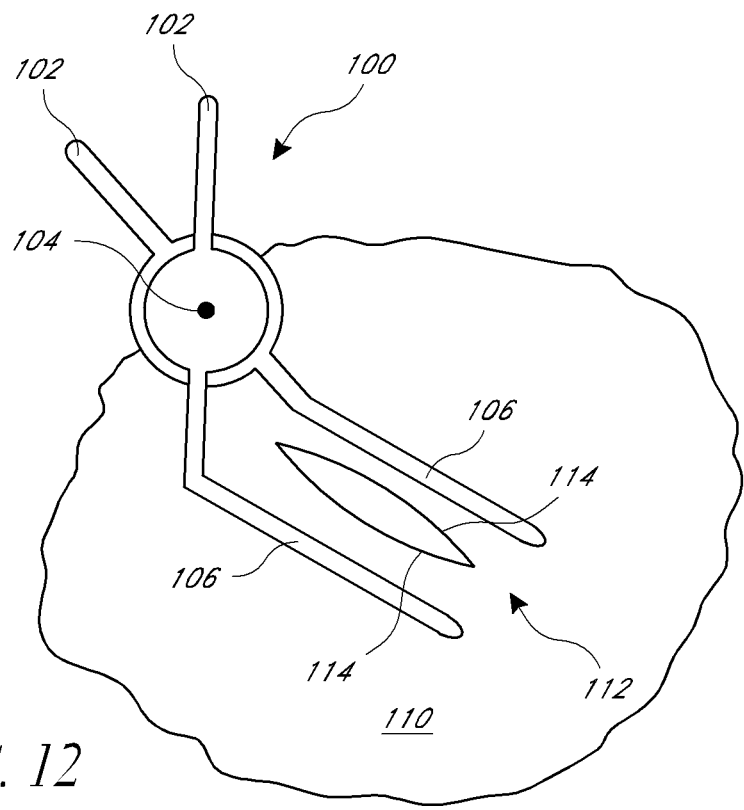
FIGS. 12-15 illustrate one embodiment of a tissue eversion system applied to a skin wound.
Figure 13:
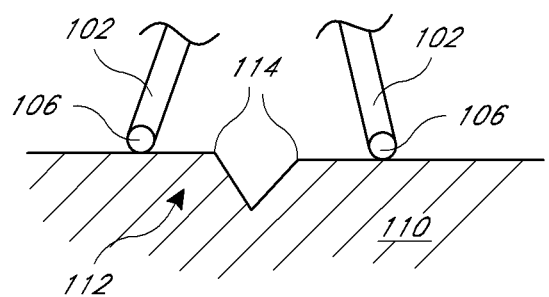

In one embodiment, the tissue eversion system 100 includes two tissue-contacting arms 102 that rotate with respect to each other about a pivot 104. Each arm 102 includes a first portion that extends in substantially the same direction as the handpiece's longitudinal axis, and second, leg portion 106, that extends at an angle of about 90 degrees with respect to the first portion. The legs 106 of tissue eversion system 100 are elongated and space apart sufficiently to be placed on opposite sides of a wound 112, as shown in FIGS. 12 and 13.

Figure 14:
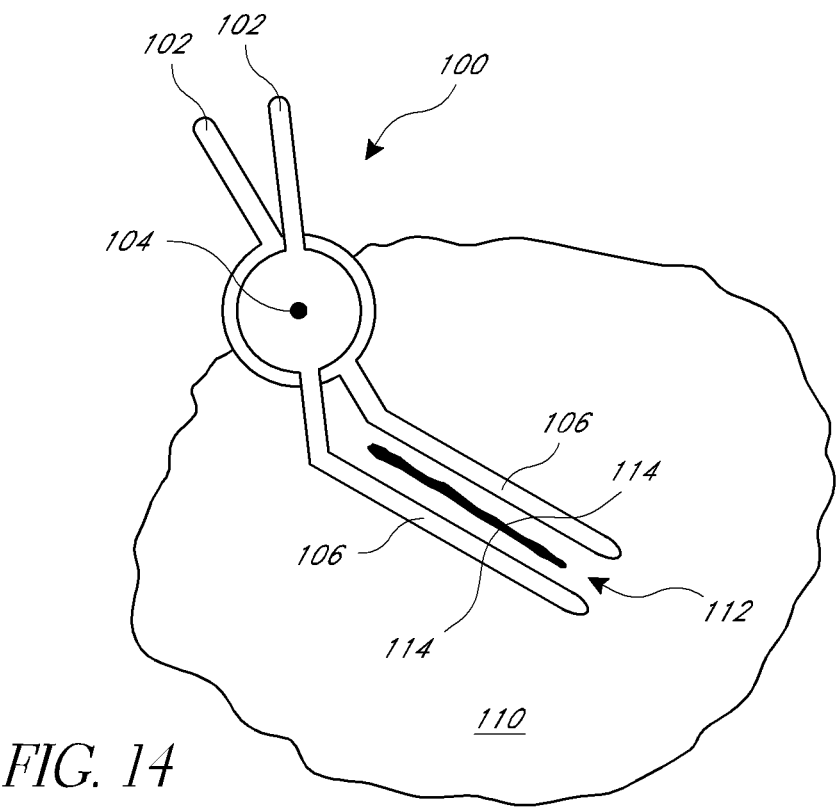
Figure 15:
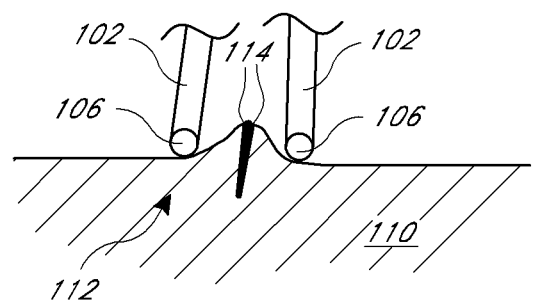

Activating the tissue eversion system's control 101 causes one or both arms 102 to rotate with respect to each other, which causes the legs 106 to move towards each other, as well. When the legs 106 are contacting tissue 110 on opposite sides of a wound 112, activating the control 101 therefore causes the opposing edges 114 of the wound to press against each other, and lift or evert a predetermined distance 116, as shown in FIGS. 14 and 15.

Electromagnetic energy is then delivered from the handpiece 66 while the tissue eversion system 100 stabilizes the wound 112 in an everted configuration. After treatment is completed and while the tissue is everted, the clinician can stitch, suture, or otherwise secure the wound in its closed configuration. Everting the tissue can eliminate the formation of dimples or other noticeable skin changes once the surgical wound 112 has healed.

In one embodiment, a method of treating tissue with an everting, electromagnetic-energy-emitting handpiece includes: aligning a tissue eversion system with a wound, everting the tissue (e.g., pinching opposing sides of the wound together to lift the edges), applying fractional laser energy to the everted wound, and suturing the wound while everted.

In another embodiment, the tissue eversion system 100 includes a sensor (not shown) that detects the spacing between the system's legs 106. For example, the sensor can include an optical sensor that responds to a material or a coating on each leg 106. In another embodiment, the sensor merely keeps track of the distance (or angle) that each arm 102 has been moved (e.g., rotated), and then calculates the spacing between the system's legs 106.

To avoid directing electromagnetic energy to the legs 106, the tissue eversion system 100 can provide an alarm to the user if it determines that the selected treatment area's size is too large, such that therapeutic energy (e.g., fractional laser light) will be directed to the tissue eversion system's legs 106. In another embodiment, the tissue eversion system 100 automatically changes the therapeutic treatment area's size automatically, for example, as the spacing between legs 106 changes.

Figure 16:
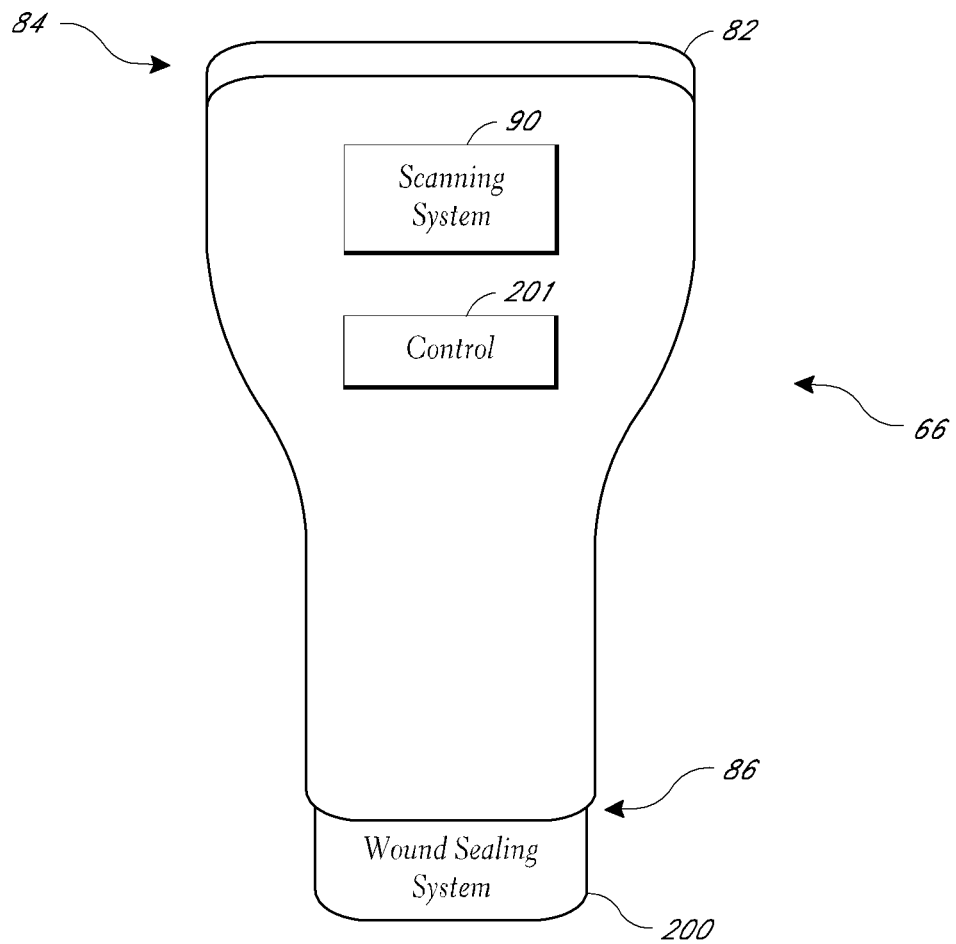
FIG. 16 is a schematic view of a handpiece configured to seal a wound before, during and/or after energy treatment, which is compatible with the electromagnetic energy source of FIG. 6.

In yet another embodiment, as illustrated in FIG. 16, a handpiece 66 includes a wound sealing system 200. When a control 201 is activated, the wound sealing system 200 seals the tissue wound after electromagnetic energy treatment, such as any of the treatments discussed above. In one embodiment, the wound sealing system includes one or more of a tissue stapler, a tissue welding system, or a tissue glue. Surgical staples advantageously hold tissue edges together without strangulating the blood supply to the tissue, which is one disadvantage of suturing a wound closed. Blood supply is not strangulated by using staples because staples enter the skin on opposite sides of the wound and protrude in a primarily linear or slightly curved direction into the tissue. On the other hand, sutures typically wrap around and circle the wound 360°, which can lead to blood supply strangulation and inferior healing.

In addition, the handpiece 66 may include more than one of the features described herein. For example, the handpiece 66 may include two or more of a medication delivery system, a tissue eversion system, and a wound sealing system. In some embodiments the handpiece 66 includes all three systems. In others, the handpiece 66 includes a tissue everting system and a wound sealing system. In such embodiments, the wound sealant may be delivered prior to eversion (e.g., apply a tissue glue prior to eversion) and/or after eversion (e.g., deliver a surgical staple or provide heat, such as laser energy, to cause tissue welding).

Although certain embodiments and examples have been described herein, it will be understood by those skilled in the art that the present inventive subject matter extends beyond the specifically disclosed embodiments to other alternative embodiments and/or uses of the invention and obvious modifications and equivalents thereof. Thus, it is intended that the scope of the present inventive subject matter herein disclosed should not be limited by the particular disclosed embodiments described above, but should be determined only by a fair reading of the claims that follow.

What is claimed is:

1. A method of reducing scar formation associated with a skin wound, comprising:
   providing a laser source;
   delivering energy from the laser source to opposing edges of a skin wound prior to initiating any sealing of the wound; and
   sealing the wound after delivering said energy.

2. The method of claim 1, wherein said laser comprises a fractional laser configured to provide a fractional laser treatment.

3. The method of claim 1, wherein said laser comprises a CO2 laser.

4. The method of claim 1, wherein said delivering energy comprises scanning a pattern of treatment spots over a treatment area around said skin wound.

5. The method of claim 4, wherein said treatment area is circular with a diameter in a range of from about 1.3 mm to about 20 mm.

6. The method of claim 5, wherein said diameter is about 10mm.

7. The method of claim 1, wherein said delivering energy comprises delivering laser light having a wavelength in a range of from about 9400 nm to about 11100 nm.

8. The method of claim 1, wherein said delivering energy comprises delivering laser light in a range of from about 5.2 J/cm2 to about 445 J/cm2.

9. The method of claim 1, wherein said delivering energy comprises delivering laser light having a pulse width in a range of from about 20microseconds to about 1000 microseconds.

10. The method of claim 1, wherein said delivering energy comprises delivering laser light having a spot density in a range of from about 5% to 100%.

11. The method of claim 1, wherein said delivering energy comprises creating a plurality of channels in the skin around the wound, each channel having a depth of about 40 microns to about 1500 microns.

12. The method of claim 1, wherein said sealing comprises suturing the wound closed.

13. The method of claim 1, wherein said sealing comprises delivering a surgical staple to skin near the skin wound to close the wound.

14. The method of claim 1, wherein said sealing comprises delivering a tissue glue to the skin wound to close the wound.

15. The method of claim 1, wherein said sealing comprises tissue welding.

16. The method of claim 1, further comprising everting the wound prior to said delivering energy from the electromagnetic energy source.

17. The method of claim 1, further comprising delivering additional energy from the electromagnetic energy source to opposing edges of the skin wound after said sealing.

18. A method of reducing scar formation associated with a skin wound, comprising:
   providing a laser system comprising a laser and a scanning handpiece optically coupled to the laser, the scanning handpiece configured to direct laser energy from the laser to a treatment area on a patient's skin to form a plurality of spots on the patient's skin within the treatment area;
   aligning an aiming beam emitted from said handpiece with respect to a wound on the patient's skin;
   activating the laser and handpiece to direct the laser energy from the laser to the treatment area on the patient's skin to form the plurality of spots on the patient's skin, wherein said treatment area comprises at least first and second portions spaced apart from each other and located on opposite sides of said aiming beam such that at least some of said laser energy is delivered to skin at or near the wound's edges; and
   sealing the wound after scanning said laser beam within the treatment area.

19. The method of claim 18, wherein said first and second portions are spaced apart from each other by about a width of the wound.

* * * * *